United States Patent [19]

Endo et al.

[11] 4,157,436
[45] Jun. 5, 1979

[54] PHOSPHORUS-CONTAINING POLYESTERS

[75] Inventors: Seiji Endo; Takao Kashihara; Akitada Osako; Tatsuhiko Shizuki; Tadashi Ikegami, all of Otsu, Japan

[73] Assignee: Toyo Boseki Kabushiki Kaisha, Japan

[21] Appl. No.: 859,104

[22] Filed: Dec. 9, 1977

Related U.S. Application Data

[62] Division of Ser. No. 730,512, Oct. 7, 1976.

[30] Foreign Application Priority Data

| Oct. 14, 1975 | [JP] | Japan | 50/124164 |
|---|---|---|---|
| Jan. 23, 1976 | [JP] | Japan | 51/6924 |
| Feb. 13, 1976 | [JP] | Japan | 51/15088 |
| Feb. 13, 1976 | [JP] | Japan | 51/15090 |

[51] Int. Cl.$^2$ ............ C08G 63/66; C08G 63/68
[52] U.S. Cl. ............ 528/167; 528/169; 528/287
[58] Field of Search ............ 260/47 P, 47 C, 936, 260/75 P, 49; 528/167, 169, 287

[56] References Cited

U.S. PATENT DOCUMENTS 3,702,878 11/1972 Saito .................. 260/936

FOREIGN PATENT DOCUMENTS 47-16436 1/1971 Japan .................. 260/936

*Primary Examiner*—Lester L. Lee

*Attorney, Agent, or Firm*—Wenderoth, Lind & Ponack

[57] ABSTRACT

The present invention relates to a flame retardant polyester having a phosphorus atom content of 500–50,000 ppm, which polyester contains a flame-retarding amount of a phosphorus containing compound represented by the following general formula:

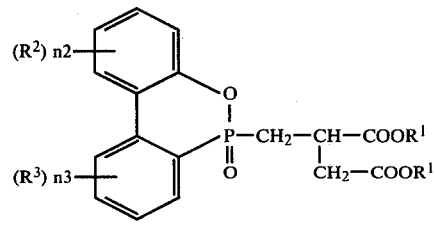

wherein each of $R^1$ is a hydrogen atom or hydrocarbon group having 1–10 carbon atoms which may contain a hydroxyl group, and both $R^1$'s may together form a dehydrated ring when both of $R^1$'s represent hydrogen atoms, each of $R^2$ and $R^3$ is a member selected from the group consisting of halogen atoms and hydrocarbon groups having 1–10 carbon atoms, and each of n2 and n3 is an integer of 0–4. Polyesters containing the claimed phosphorus containing compounds are characterized by exhibiting excellent flame retardancy and at the same time, the physical properties of the polyesters are not impaired by incorporation of the phosphorus compound therein.

3 Claims, No Drawings

PHOSPHORUS-CONTAINING POLYESTERS

This is a division of application Ser. No. 730,512, filed Oct. 7, 1976.

The present invention relates to new phosphorus-containing compounds. More particularly, the invention is concerned with new phosphorus-containing compounds which show an excellent compatibility and heat stability when added to high molecular weight compounds such as polyesters or polyamides to produce shaped products, and which are capable of providing a high flame retardancy.

In recent years, emphasis has been placed on the necessity for rendering flame-retardant various shaped products including fibers from the standpoint of human importance, and much effort has been directed to this purpose. To impart flame retardancy to shaped products produced from linear polyesters, various proposals have been made: for example a process wherein, upon the production of the polymer, a flame retardant substance is added for the purpose of copolymerization or blending; a process wherein, upon the manufacture of shaped products, a flame retardant substance is kneaded into the linear polyester; or a process wherein flame retardancy is imparted by after-treating shaped products from the linear polyester. Among these processes, when industrial value is taken into consideration, the process in which a flame retardant substance is added upon the production of the polyester for the purpose of copolymerization is the most advantageous from the viewpoint that it is easiest and various properties of the shaped products obtained are not impaired. For this purpose, various phosphorus compounds have been heretofore used. When phosphorus compounds are added upon the production of polyesters, it has been common practice to use phosphoric acid esters such as triphenyl phosphate, or phosphonic acids such as benzenephosphonic acid derivatives. However, when using such compounds, there have been various problems: the phenomenon of a catalyst activity loss may occur upon the production of polyesters; ether linkages may be formed to lower the melting point of the resulting polymer or they may cause gelation of the polymer. In addition, because of the large dissipation of phosphorus compounds from the polymerization system, it is difficult to obtain a polymer having excellent flame retardancy. Moreover the environment is polluted by the dissipation of phosphorus compounds.

To solve such problems, we made a research for suitable phosphorus compounds. As a result, we have found that, by using the later-mentioned phosphonic acid derivatives having a particular structure, linear polyesters can be produced without any substantial problem in the same way as in the polymerization of the usual polyesters. The polyesters thus obtained have a very small amount of ether linkage and excellent flame retardancy (Japanese patent application 7072/1975). The above-mentioned phosphonic acid derivatives have a structure shown by the following general formula (II):

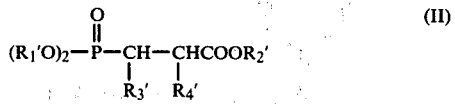

wherein $R_1'$ and $R_2'$ are each a monovalent hydrocarbon group having 1-18 carbon atoms; and $R_3'$ and $R_4'$ are each a hydrogen atom or a hydrocarbon group having 1-4 carbon atoms.

However, when the phosphonic acid derivatives represented by the general formula (II) are added upon the production of flame retardant polyesters, there is a possiblity of causing a cross-linking reaction because the phosphonic acid derivatives are trifunctional compounds. Therefore, it is inevitable that cross-linked portions may be mixed in the resulting product. Therefore, when such flame retardant polyesters are melt-shaped into products such as fibers or films, there is a tendency that the physical properties of the shaped products or the operational efficiency may be lowered.

To improve such a situation, we further made a research for phosphorus compounds which will provide excellent flame retardant polyesters and which have no cross-linking action. As a result, we have found very suitable compounds. This finding led to the accomplishment of the present invention.

The above-mentioned compounds are new phosphorus-containing compounds represented by the following general formula (I):

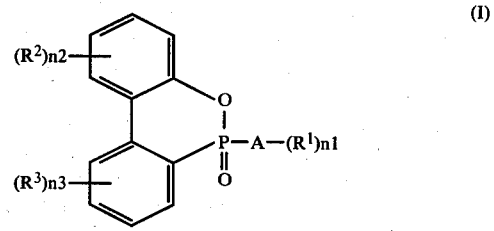

wherein $R^1$ is an ester-forming functional group selected from the class consisting of $—COOR^4$, $—OR^5$ and $—OCOR^6$ wherein $R^4$ is a hydrogen atom, a carbonyl group or a hydrocarbon group having 1-10 carbon atoms which may contain a hydroxyl group or a carboxyl group and $R^5$ is a hydrogen atom or a hydrocarbon group having 1-10 carbon atoms which may contain a hydroxyl group or a carboxyl group and $R^6$ is a hydrocarbon group having 1-10 carbon atoms which may contain a hydroxyl group or a carboxyl group; $R^2$ and $R^3$ are the same or different groups and are selected from halogen atoms, hydrocarbon groups having 1-10 carbon atoms and $R^1$, respectively; A is a divalent or trivalent hydrocarbon group having 1-8 carbon atoms; n1 is an integer of 1 or 2, n2 and n3 are each an integer of 0-4.

Concrete examples of producing the phosphorus-containing compounds of the present invention will be described hereinafter, but said compounds can be produced, for example, by the processes shown in the following: they can be produced by reacting 9,10-dihydro-9-oxa-10-phosphaphenanthrene-10-oxide (hereinafter referred to as DOP) or its benzene nucleus substituted compound thereof with an unsaturated compound having an ester-forming functional group, or by esterifying with a diol or a dicarboxylic acid at the same time with or after the above-mentioned reaction. As regards the above-mentioned unsaturated compound, it is preferable to select it from dicarboxylic acids such as maleic acid, fumaric acid, itaconic acid, acrylic acid, methacrylic acid, mesaconic acid, citraconic acid, glutaconic acid, etc. or their anhydrides and esters, but oxycarboxylic acids such as brantenolic acid or unsaturated glycols such as 2-butene-1,4-diol and 3-butene-1,2-diol may be used. As the particularly preferred unsaturated compounds in the present invention, itaconic acid or lower alkyl esters or the anhydride of itaconic acid may be mentioned.

The above-mentioned DOP or its benzene nucleus substituted compounds can be synthesized from 2-hydroxybiphenyl or its nucleus substituted compounds and phosphorus trichloride, as shown in Japanese Pat. No. 45397/1974. To produce the phosphorus-containing compounds of the present invention, it is particularly preferable to use the compound having no substituent group at the benzene nuclei, namely the compound of the formula (I) wherein n2 and n3 are both 0 (i.e. DOP). In the reaction of DOP or its benzene nucleus substituted compound thereof with the above-mentioned unsaturated compound, it is preferable to react them so that the molar ratio of the former to the latter is nearly 1:1, but it is also possible to use any one of them in some excess.

As an example of the processes for producing the phosphorus-containing compounds of the present invention, a concrete explanation is given for the case of using DOP and dimethyl itaconate as the starting compounds: after the starting compounds are mixed at room temperature, the mixture is heated under stirring at a temperature above 100° C., preferably between 120° and 200° C. under an inert gas atmosphere, whereby the object substance can be produced. Cases most frequently met with are those where the use of a metal alkoxide such as sodium methoxide, sodium ethoxide, potassium ethoxide, etc. as the catalyst, is advantageous for increasing the reaction speed. In order to suppress any side-reaction, a lower alcohol such as methanol, ethanol, isopropanol, n-butanol, etc. may be present in the reaction system.

In the concrete examples of the new phosphorus-containing compounds of the present invention, $R^1$ in the general formula (I) is a carboxyl group, an alkyl ester of a carboxyl group having 1-7 carbon atoms, a cycloalkyl ester, an aryl ester, a hydroxyl group, a hydroxyalkoxycarbonyl group having 1-7 carbon atoms or a group represented by

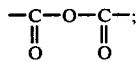

and n1 is preferably 2. When n1 is 2, $R^1$ may be the same or different groups. As regards $R^2$ and $R^3$, a halogen atom such as a chlorine atom, a bromine atom, an alkyl group having 1-6 carbon atoms, a cycloalkyl group, an aryl group and the above-mentioned monovalent groups of $R^1$ may be mentioned as preferred ones. As the preferred examples of A, there may be mentioned lower alkylene groups such as methylene, ethylene, 1,2-propylene, 1,3-propylene, etc.; arylene groups such as 1,3-phenylene, 1,4-phenylene, etc.; divalent groups having arylene such as 1,3-xylylene, 1,4-xylylene,

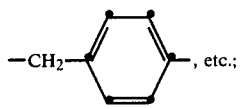

a trivalent group represented by

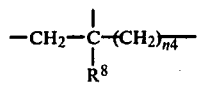

(wherein $R^8$ stands for a hydrogen atom, or a lower alkyl group such as methyl, ethyl, etc., and n4 stands for 0 or 1) and

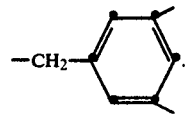

The above-mentioned hydrocarbon groups may be substituted by a halogen atom such as a chlorine atom, a bromine atom, etc. As for A, a trivalent group is preferable.

Among the concrete examples of the phosphorus compounds represented by the above-mentioned general formula (I), the following compounds may be mentioned:

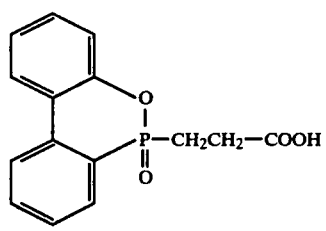

(a)

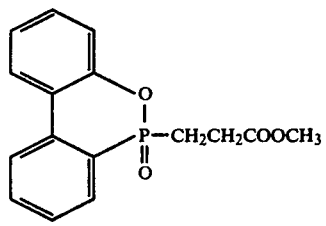

(b)

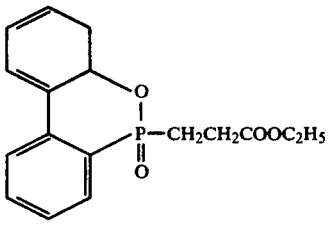

(c)

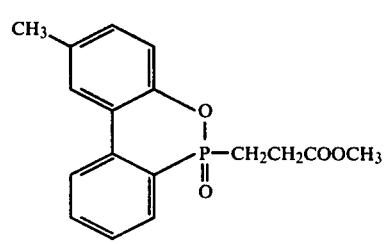

(d)

-continued
(e) 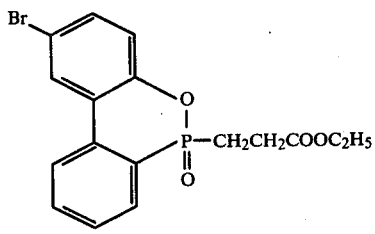
(f) 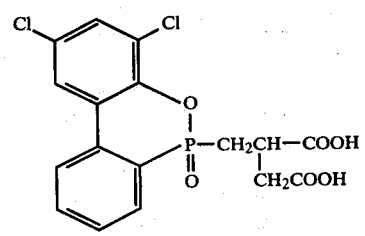
(g) 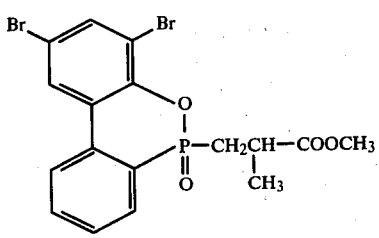
(h) 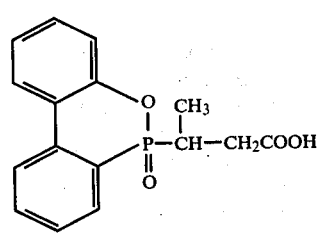
(i) 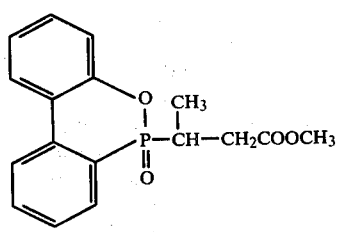
(j) 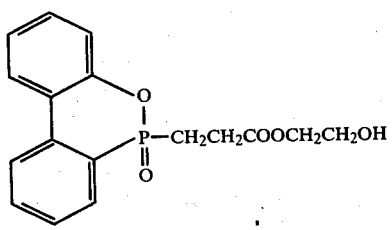
(k) 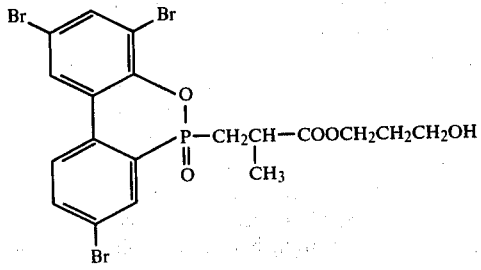
-continued
(l) 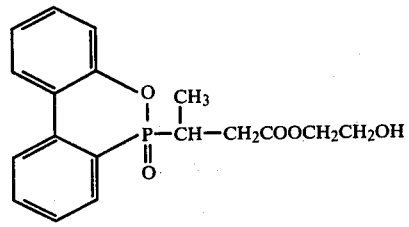
(m) 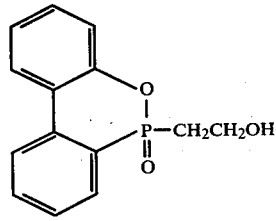
(n) 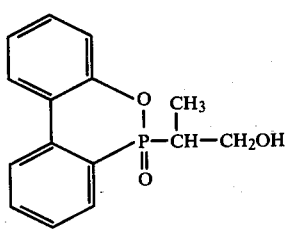
(o) 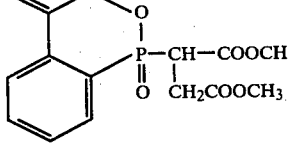
(p) 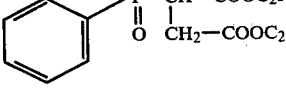
(q) 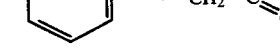
(r) 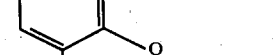

(s) 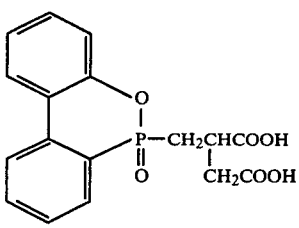

(t) 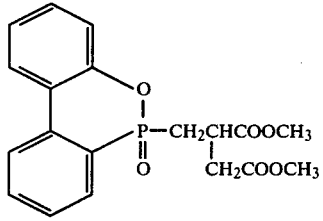

(u) 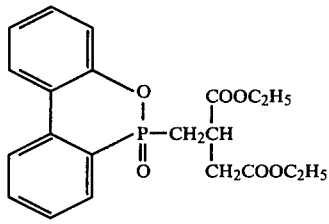

(v) 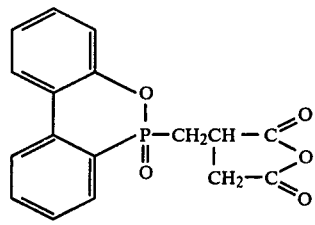

(w) 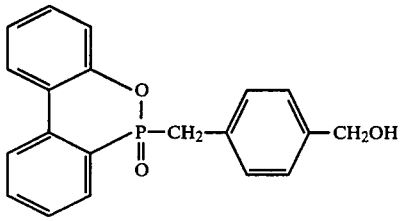

(x) 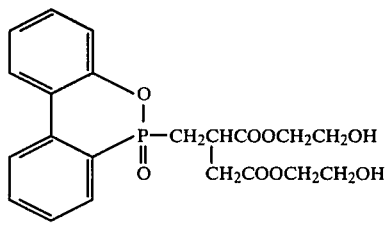

(y) 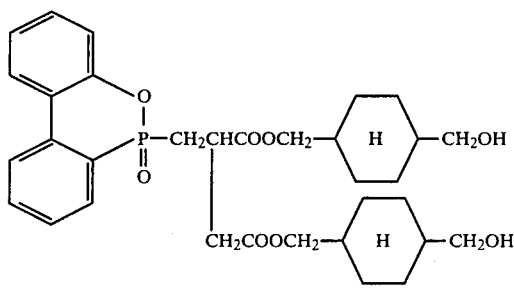

(z) 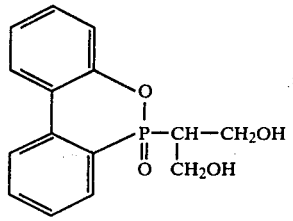

By polycondensing a phosphorus-containing compound of the present invention with a dihydric alcohol, a dihydric phenol or a divalent amine, or by copolycondensing a phosphorus-containing compound of the present invention with a dihydric alcohol, a dihydric phenol, a divalent amine or/and another dicarboxylic acid or a derivative thereof, it is possible to easily produce a phosphorus-containing high molecular weight compound such as polyester, polyamide, polyurethane, polyether, etc.

Furthermore, it is possible to utilize the phosphorus-containing compounds as flame retardants for various high molecular weight compounds. Namely, the above-mentioned phosphorus-containing flame retardants are obtained by reacting at least one kind of unsaturated compound containing at least one ester-forming functional group, DOP or its benzene nucleus substituted compound thereof, and at least one kind of the ester-forming compounds selected from dicarboxylic acids or their ester-forming derivatives, diols or their ester-forming derivatives, and oxycarboxylic acids or their ester-forming derivatives. Upon producing the above-mentioned phosphorus-containing flame retardants, it is particularly preferable in the present invention to employ the process wherein a phosphorus-containing compound is first produced by reacting the above-mentioned unsaturated compound with DOP or a benzene nucleus substituted derivative thereof and then the phosphorus-containing compound is reacted with at least one kind of the above-mentioned ester-forming compounds to obtain the intended flame retardant. Especially when the flame retardant is applied to polyesters, after the unsaturated compound containing ester-forming groups and DOP are dissolved in a diol, it is convenient to add the resulting solution directly to the polyester polymerization process.

The above-mentioned ester-forming compound is suitably selected from the dicarboxylic acid component, diol component and oxycarboxylic acid component used upon the production of the polyester. Namely, as the dicarboxylic acids or their ester-forming derivatives used for the production of the flame retardants, there may be used any of the ester-forming derivatives such as aromatic dicarboxylic acids, aliphatic dicarboxylic acids, alicyclic dicarboxylic acids or their alkyl esters.

Upon producing the flame retardants of the present invention by reacting an ester-forming compound as mentioned above, it is desirable to adjust the amount of use of each starting material so that the phosphorus content in the resulting flame retardant should be above 2,000 ppm, preferably within the range of 5,000 to 90,000 ppm. This is because, if the phosphorus content is lower than 2,000 ppm, the flame retardancy imparting power of the resulting flame retardant is undesirably lowered. Vice versa, if the phosphorus content in the flame retardant is too high, it is impossible to obtain a satisfactory product even by the process which will be described hereinafter.

The process for producing the flame retardants of the present invention are not particularly limited except that the phosphorus-containing compound and the ester-forming compound are used so that the phosphorus content in the resulting flame retardant should be within the above-mentioned range. However, the flame retardants can be produced as described hereinafter, for example.

Namely, in the present invention, it is desirable to select such a phosphrus-containing compound that $R^1$ in said compound is a carboxyl group, carboxylate group, or in the form of acid anhydride. When using a phosphorus compound whose $R^1$ is a carboxylate group, it is necessary to produce the object flame retardant by using a diol as the ester-forming compound, namely by the so-called transesterification reaction. As the conditions for this transesterification reaction, it is possible to employ conditions nearly in accordance with the conditions under which aromatic polyesters are produced. Namely, the object flame retardant can be produced by heating the reaction mixture under reflux within the temperature range of from about 50° to 280° C. under atmospheric pressure in the presence of a compound of metals selected from zinc, manganese, titanium, cobalt, magnesium, etc. as the catalyst for the transesterification reaction.

Where the phosphorus-containing compound is in the form of free acid or anhydride, it is possible to produce the flame retardants of the present invention by using a diol as the ester-forming compound and in accordance with the so-called direct esterification used upon producing aromatic polyesters. Namely, the object substance can be produced by heating the reaction mixture within the temperature range of from about 100° C. to about 280° C. under atmospheric pressure or under an increased pressure up to 5 kg/cm$^2$ in the presence of a same metal compound as in the case of the above-mentioned transesterification reaction or a tin compound, as the esterification catalyst. Either in the case of this method or in the case of the above-mentioned transesterification reaction, when the reaction system is brought to a somewhat higher temperature and a reduced pressure at the last stage of the reaction, the resulting flame retardant can have a higher softening point, so that the compatibility of this flame retardant with high molecular weight compounds is improved and thus this procedure is very useful. Even flame retardants having a softening point of 30° C. can have a sufficient utility, but those having a softening point higher than 70° C. are easier in handling.

The flame retardants of the present invention may be produced by other processes, but said flame retardants can be produced more easily by the above-mentioned processes, and the physical properties of the flame retardants so produced are very satisfactory.

The flame retardants of the present invention thus produced not only can provide excellent flame retardancy to high molecular weight polymers such as polyamides, polyolefins, polystyrenes, polyacrylonitriles and polyesters, but in addition, when mixed particularly with polyesters to produce shaped products, they have no action of lowering the degree of polymerization of the polyesters, so that it is extremely rare that they exert adverse effects on the physical properties and color of the resulting polyester shaped products.

The flame retardants of the present invention have very good compatibility with polyesters, presumably because they have an analogous chemical structure to the fundamental skeleton of polyesters. Therefore, they can be used for producing various excellent flame retardant shaped products by mixing with polyesters by a simple operation.

As mentioned earlier, the phosphorus-containing compounds and phosphorus-containing flame retardants of the present invention are very useful for producing flame retardant polyesters having excellent properties by mixing them with polyesters. Especially, even at high temperatures of the production system of polyesters, the phosphorus-containing compounds of the present invention cause no substantial heat decomposition or gelation, so that the resulting flame retardant polyesters have an excellent color tone. Also, the mechanical properties thereof are so good that there is no perceptible difference from the properties of those produced without using the phosphorus-containing compounds of the present invention. When flame retardant polyesters are produced using the phosphorus-containing compounds of the present invention, it is desirable that the content of phsphorus atoms in the resulting polyester should be 500 to 50000 ppm. Particularly in the case of polyesters for producing fibers, it is preferable to use the phosphorus-containing compound in such a manner that the phosphorus atom content should be 1,000 to 10,000 ppm.

Where the amount of use of the above-mentioned phosphorus compounds is smaller than the above mentioned range, it becomes difficult to obtain polyesters having the desired flame retardancy. Vice versa, where the amount of use is larger than that range, not only the physical properties of the resulting polyester are impaired, but also the production efficiency upon producing the polyester is lowered. Theefore such amounts of use are not desirable.

Upon producing flame retardant polyesters in the present invention, the method of adding the above-mentioned phosphorus-containing compounds to the polyester production system is not particularly limited. Namely, for example, when polyesters are produced by the so-called transesterification process of dicarboxylic acid diester and diol, the the above-mentioned phosphorus-containing compounds or phosphorus-containing flame retardants may be added upon the transesterification reaction, or they may be added before the polycondensation reaction after the transesterification reaction, or at a relatively early stage of the polycondensation reaction. Also, upon producing polyesters by the so-called esterification process of dicarboxylic acid and diol, they may be added at any stage of esterification. In the present invention, it is desirable to add the above-mentioned phosphorus-containing compounds to the reaction system as a solution or a dispersion in a monohydric alcohol such as methanol, ethanol, etc. or in an adihydric alcohol such as ethylene glycol, propylene glycol, butan diol, etc.

Also, it is possible to prepare polyester master pellets containing more than about 2,000 ppm of the phosphorus-containing flame retardant and mix them with the ordinary pellets to supply the mixture to the shaping step.

Among the dicarboxylic acids used for the production of flame retardants or flame retardant polyesters, the aromatic dicarboxylic acids include for example terephthalic acid, isophthalic acid, 1,4-naphthalenedicarboxylic acid, 2,6-naphthalendicarboxylic acid, 1,2-bis(4-carboxyphenoxy)ethane, which are particularly preferred ones, and in addition, tetrabromoterephthalic acid, 2,2-bis(4-carboxyphenyl)propane, bis(4-carboxyphenyl)sulfone, bis(4-carboxyphenyl)ether, 2,2-bis(3,5-dibromo-4-carboxyphenyl)propane, 4,4'-dicarboxyphenylbiphenyl, and sodium 3,5-dicarboxybenzenesulfonate.

Among other dicarboxylic acids, there may be mentioned aliphatic or alicyclic dicarboxylic acids such as adipic acid, suberic acid, azelaic acid, sebacic acid, hexahydroterephthalic acid, etc. or their mixtures.

On the other hand, among the diol compounds, there may be mentioned ethylene glycol, 1,2-propylene glycol, trimethylene glycol, butan diol, neopentylene glycol, 1,4-cyclohexane diol, 1,4-cyclohexane dimethanol, diethylene glycol and polyethylene glycol. When the diols represented by the following general formulae are used as copolymerization components, the flame retardancy of the resulting polyester becomes more excellent.

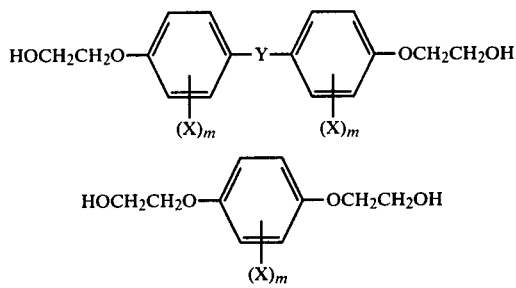

wherein X represents a halogen atom, Y represents an alkylidene group, cycloalkylidene group, arylalkylidene group, —S—, —SO—, —SO$_2$— or —O—, and m represents an integer of 1–4.

Also, the carbonate of the above-mentioned glycols or ethyelne oxide, propylene oxide, etc. may be used.

Among the oxycarboxylic acid or its ester-forming derivative components, there may be mentioned for example 4-oxybenzoic acid, 4-hydroxyethoxybenzoic acid, oxypivalic acid and their alkyl esters.

In the present invention, the flame retardant polyesters are produced from the above-mentioned dicarboxylic acid components, diol components and the phosphorus compounds represented by the general formula (I), or from oxycarboxylic acid components and the phosphorus compounds represented by the general formula (I), but the conditions for the production of polyesters, for example the conditions of transesterification or esterification and polycondensation can be in accordance with the conventional known process. For example, in the case of producing the flame retardant polyesters of the present invention using terephthalic acid as the dicarboxylic acid component and ethylene glycol as the diol component, the transesterification reaction is carried out at 150°–240° C. using, as the catalyst, a conventional alkali metal, alkali-earth metal, or a compound of metals such as zinc, manganese, cobalt, titanium, etc. On the other hand, the esterification reaction is carried out, using as the catalyst nearly the same metal compounds as used in the transesterification reaction, at a pressure from atmospheric pressure to 5 kg/cm$^2$-G and at a temperature between 200° and 280° C., to obtain the object reaction product, which is then polycondensed under a high vacuum below 1 mm Hg at a temperature between 250° and 320° C. in the presence of a compound of metals such as antimony, germanium, titanium, etc. to obtain the object polyester. Therefore, one of the greatest features of the present invention is that polyesters having excellent flame retardancy can be produced by following the conventional known process nearly in every respect.

When the flame retardant polyesters are produced in the present invention, the phosphorus compounds represented by the above-mentioned general formula (I) are extremely stable against heat in comparison with the usually used phosphorus compounds, presumably because, in the phosphorus compounds represented by the formula (I), the phosphorus atom constitutes a ring member. Therefore, since no substantial side-reaction occurs such as gelation reaction resulting from the heat decomposition of the phosphorus compound upon the polycondensation reaction, the polyesters obtained by the process of the present invention are excellent in color tone, and have better physical properties than conventional flame retardant polyesters. Accordingly, it is possible to produce shaped flame retardant products having excellent properties from the polyesters in question.

When the phosphorus compound represented by the above-mentioned general formula (I) has only one ester-forming functional group, this phosphorus compound can act as a terminal stopper, so that cases may occur where the use in combination with a known polyfunctional compound for example pentaerythritol or a trifunctional carboxylic acid is preferable.

It does not depart from the spirit of the present invention to use the usual additives, for example the so-called ether linkage inhibitor such as organic amines and organic carbonic acid amides; pigments such as titanium oxide and carboxylic black; stabilizers, plasticizers, antistatic agents, etc. upon producing the flame retardant polyesters according to the present invention.

As mentioned above, the flame retardant polyesters obtained according to the present invention have various excellent properties in addition to flame retardancy, so that they are used not only for fibers but also for films, boards and other shaped products.

The present invention will be more concretely explained with reference to examples of the preparation of the phosphorus-containing compounds and phosphorus-containing flame retardants, and to examples of the production of flame retardant polyesters. In these examples, the parts and percentages are by weight. The intrinsic viscosity was obtained from the values measured in a mixed solvent of phenol and 1,1,2,2-tetrachloroethane (weight ratio 3:2) at 30° C. The phosphorus content was measured colorimetrically after the sample was heat-decomposed with sulfuric acid, nitric acid and perchloric acid and color-developed with ammonium molybdate and hydrazinium sulfate. The content of trivalent phosphorus was measured by iodometry after the sample was dissolved in isopropyl alcohol. The refractive index was measured by means of an Abbé's refractometer at 30° C. The viscosity was measured with a Brookfield viscosimeter at 30° C. The acid value was measured by titrating an ethyl alcohol solution of the sample with an aqueous 1/10 N sodium hydroxide solution in the presence of a phenolphthalein solution as the indicator. As for the measurement of the saponification value, the sample was saponified with a ½ N potassium hydroxide/95% ethyl alcohol solution at 75° C. for 60 minutes and the saponified solution was titrated with a ½ N hydrochloric acid solution in the presence of a phenolphthale in solution as the indicator. The infrared absorption spectrum was measured from a potassim bromide plate on which the sample was spread. The nucleus magnetic resonance absorption spectrum (hereinafter abbreviated as NMR) was measured from a solution of the sample in 10 weight % heavy-hydrogenated chloroform by means of a Varian A-60 apparatus (60 M Hz; produced by Varian Co.) under the conditions of a filter width of 1 cycle/sec., a sweep time of 250 seconds and a sweep width of 500 cycles/sec., at 70° C. with TMS as the inner standard. As for the high-speed liquid chromatograph, a Waters High-Speed Chromatographic Apparatus (Waters Co.) was used with Microbondapack C-18 as the packing agent and methyl alcohol as the liquid phase (at the rate of 1 ml/min.), and an ultraviolet absorption detector was used for the detection. The flame retardancy was measured as follows: Yarns obtained by spinning and drawing a polyester in the usual way were knitted into a tricot cloth. One gram of the tricot was rounded in a length of 10 cm and was inserted into a wire coil having a diameter of 10 mm. While the tricot in the wire coil was held at the angle of 45°, it was ignited at the lower end. When the fire died out by removing the fire source, the ignition was repeated. The number of the ignitions required for burning down the whole sample completely was obtained for five samples. The flame retardancy was expressed by the average number of ignitions.

PREPARATION 1

Into a four-necked flask equipped with a stirrer, a reflux condenser, a thermometer and a dropping funnel, 503 g. 9,10-dihydro-9-oxa-10-phosphaphenanthrene-10oxide (DOP), 200 g. methyl acrylate and 440 g. methyl alcohol were charged. With the flask held on a water bath maintained at 35° C., a 1 N methyl alcohol solution of sodium methoxide was added dropwise from the dropping funnel. While taking care so that the temperature of the reaction system did not exceed 65° C., 35 g. of the above-mentioned methyl alcohol solution was added dropwise in 10 minutes. The thus-obtained solution was slightly brown. It was confirmed from iodometric analysis that the reaction rate of DOP was 99.3%, and from gas chromatographic analysis that the reaction rate of methyl acrylate was 98.9%.

The solution was heated to 100° C. at a reduced pressure below 1 mm Hg for 2 hours to remove volatile matter including methanol. The residue at room temperature was a slightly brown viscous liquid (A), and the remaining ratio of the residue was 59.8%. Its refractive index ($n_D^{30}$) was 1.6071. By distilling a part of the liquid (A) at 220° C. under 0.2 mm Hg, the main fraction was obtained, which had a refractive index of 1.6068. From the analysis by infrared absorption spectrum and NMR, it was found that this main fraction had the following structure. The values obtained by the elemental analysis of this main fraction were: P=10.20%, C=63.62% and H=5.01% which coincided well with the theoretical values: P=10.25%, C=63.57% and H=5.00%.

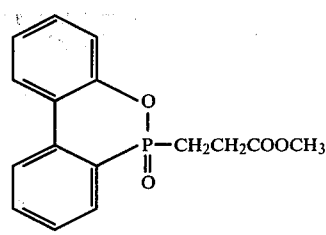

PREPARATION 2

508 g. of DOP, 372 g. of dimethyl itaconate and 390 g. of methyl alcohol were charged into the four-necked flask as used in Preparation 1. In the same way as in Preparation 1, 33 g. of a 1 N methyl alcohol solution of sodium methoxide was added dropwise in 10 minutes, whereby the reaction was made to proceed. The solution thus obtained was slightly brown. From the analysis by iodometry, it was confirmed that the reaction rate of dimethyl itaconate was 98.8%.

This solution was removed from volatile matter by heating at 100° C. under a reduced pressure below 1 mm Hg for 2 hours. The residue was a glassy semi-solid (B) at room temperature and the remaining ratio was 66.7%. The acid value of the semi-solid (B) was 0 meq/kg and the phosphorus content by elemental analysis was 8.24%. By recrystallizing the semi-solid (B) from ethylene glycol, a white solid (B) having a melting point of 88.1° C. was obtained.

The infrared spectrum of this white solid (B) had maximum absorption values at 3060, 3000, 2945, 1740, 1600, 1480, 1440, 1375, 1280, 1260, 1240, 1210, 1200, 1170, 1120, 914, 760, 720, 620, 600, and 530 cm$^{-1}$, respectively. The $\tau$ values by NMR measured in CDCl$_3$ at 60° C. were 2.0–3.0, 6.4–6.5, and 7.0–8.0. The values of elemental analysis were: P=8.28%, C=61.03% and H=5.14%, which coincided well with the theoretical values P=8.27%, C=60.98% and H=5.12% of the following structure.

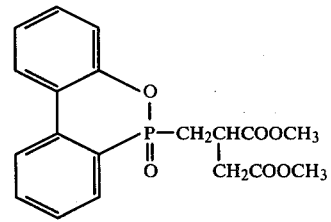

The acid value of the solid (B) was 0.00 meq/kg and the saponification value was 7.99 eq/kg (theoretical value: 8.01 eq/kg).

PREPARATION 3

497 g. DOP, and 400 g. dimethyl itaconate were charged into a four-necked flask equipped with a stirrer, a reflux condenser, a thermometer and a nitrogen inlet tube. While the flask was held on an oil bath maintained at 150° C., the reaction mixture was allowed to react under stirring for 4 hours under a nitrogen atmosphere. Thereafter, unreacted dimethyl itaconate was distilled at 150° C., and under a reduced pressure below 1 mm Hg spending 2 hours. The thus-obtained substance at room temperature was a colorless transparent semi-solid (C) having a boiling point of 235°–237° C./0.08 mm Hg. It was found that the remaining ratio of unreacted DOP was 0.5%, from iodometric analysis, and the phosphorus content by elemental analysis was 8.26% and the acid value was 4 meq/kg. After the recrystallization of the semi-solid (C) from ethylene glycol, a white solid (C) having a melting point of 88.2° C. was obtained. It was confirmed that this solid (C) was a compound having the following structure from the analysis by infrared absorption spectrum and NMR spectrum. The phosphorus content by elemental analysis was 8.29% which coincided well with the theoretical value of 8.27%.

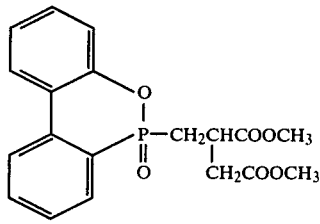

PREPARATION 4

540 g. DOP and 316 g. itaconic acid were charged into the four-necked flask as used in Preparation 3, and the reaction mixture was reacted in the same way as in Preparation 3, and then the volatile matter was distilled off. The thus-obtained substance was a colorless transparent solid (D) having a melting point of 86° C. It was confirmed from the analysis by iodometry that the remaining ratio of unreacted DOP was 0.7%, and from elemental analysis, that the phosphorus content was 8.93%. By recrystallizing the solid (D) from dioxane, a white solid having a melting point of 189.4° C. was obtained. The infrared spectrum of this solid had a maximum absorption at 1712 cm$^{-1}$ which was due to $\nu$ c=0 of carboxylic acids. NMR showed absorption at a $\tau$ value of 7.0-7.3 due to H of —P—CH$_2$—. The values of the elemental analysis were: P=8.95%, C=58.88% and H=4.39%, which coincided well with the values P=8.94%, C=58.96% and H=4.37% of the following structure:

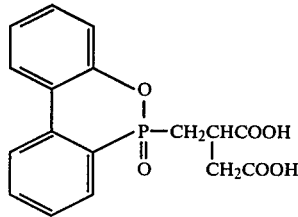

PREPARATION 5

346 g. of the solid (D) produced in Preparation 4 and 346 g. ethylene glycol were charged into a four-necked flask equipped with a stirrer, a thermometer, a nitrogen inlet tube and a distillation apparatus. With the flask held on an oil bath maintained at 200° C., the reaction mixture was reacted under a nitrogen atmosphere for 4 hours while the water formed was distilled off with ethylene glycol. A total of a 65 g. solution containing 36 g. water and 29 g. ethylene glycol was finally distilled out. The thus-obtained solution was a colorless transparent viscous liquid (E) at room temperature which had the structure described hereinafter. The phosphorus content by elemental analysis of the liquid (E) was 5.11%. The content of trivalent phosphorus by iodometry was 0.01%, the refractive index 1.5362, the viscosity 24.0 poises, the acid value 0.09 eq/kg, and the saponification value 4.77 eq/kg. The ethyelene glycol esterification ratio of the carboxylic acid calculated from these values was 98%. The infrared absorption spectrum had a maximum absorption at 1740 cm$^{-1}$ due to $\nu$ c=0 of carboxylic acid esters. NMR showed an absorption at the $\tau$ value of 7.0-7.3 due to H of —P—CH$_2$—.

30 parts of the liquid (E) thus obtained was dissolved in 2 liters of cold water. The solution was filtered to remove undissolved viscous liquid. The thus-obtained aqueous solution was charged into a separating funnel and extracted with 50 ml chloroform three times. The chloroform solution was washed with 50 ml water 3 times. The thus-obtained chloroform solution was put into a round bottom flask and the volatile matter was distilled off with an evaporator at 60° C. under a reduced pressure of 0.1 mm Hg finally. The content thus obtained was a colorless, transparent, highly viscous liquid at room temperature. This liquid is named liquid (e).

The phosphorus content of this liquid (e) was 7.12%; the trivalent phosphorus content 0.00%; the elemental analysis values C=58.02, H=5.33%; the acid value 0.00 eq/kg; the saponification value 6.88 eq/kg; and the esterification value was 100%. The infrared spectrum had a maximum absorption at 1740 cm$^{-1}$ due to $\nu$ c=0 of carboxylic acid esters. NMR had absorption at the $\tau$ values of 1.8-2.8; 5.6-6.0; 6.0-6.2; 6.2-6.5; 6.5-7.0; 7.0-7.3 and 7.3-7.8 due to H of

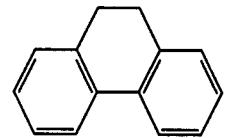

nucleus, —COOCH$_2$—, OH, —CH$_2$O—, —CH—, P—CH$_2$— and —CH$_2$—, respectively, and the absorption ratio of these was 8:4:2:4:1:2:2. As regards the high-speed liquid chromatograph, only a single peak was observed after 180 seconds. From these analytical values, it was found that the liquid (e) is 10-[2,3-di(2-hydroxyethoxy)carbonylpropyl]-9,10-dihydro-9-oxa-10-phosphaphenanthrene-10-oxide having the following structure:

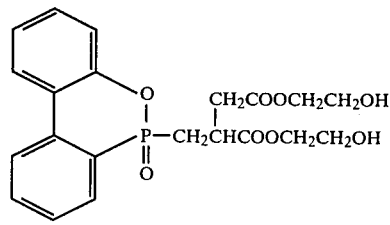

PREPARATION 6

216 g. DOP, 130 g. itaconic acid and 346 g. ethylene glycol were charged into a four-necked flask as used in Preparation 5. With the flask held on an oil bath maintained at 160° C., the reaction mixture was allowed to react for 2 hours under a nitrogen atmosphere while the water formed was distilled out with ethylene glycol, and finally a 33 g. solution in total containing 30 g. water and 3 g. ethylene glycol was distilled out. The thus-obtained solution was a colorless, transparent, viscous liquid (F) at room temperature. The phosphorus content of this liquid (F) was 4.50%, the trivalent phosphorus content 0.04%, the refractive index 1.5227, the viscosity 9.7 poises, the acid value 0.17 eq/kg and the saponification value was 4.42 eq/kg. The ethylene glycol esterification ratio of the carboxylic acid calculated from these values was 95%. The infrared absorption spectrum had a maximum absorption at 1740 cm$^{-1}$, and NMR had an absorption at the $\tau$ value of 7.0–7.3.

30 parts of the liquid (F) thus obtained was extracted with chloroform, washed with water and dried in the same way as in Preparation 5, whereby a liquid was obtained which was colorless, transparent and highly viscous at room temperature. This liquid is named (f). The phosphorus content of this liquid (f) was 7.15%, the trivalent phosphorus content 0.00%, the elemental analysis values C=58.09% and H=5.27%, the acid value 0.00 eq/kg, the saponification value 692 eq/kg and the esterification ratio 100%. The infrared spectrum had a maximum absorption at 1740 cm$^{-1}$. The NMR had absorption at the $\tau$ values of 1.8–2.9, 5.6–6.0, 6.0–6.2, 6.2–6.5, 6.5–7.0, 7.0–7.3 and 7.3–7.8, and their absorption ratio was 8:4:2:4:1:2:2. As regards the high speed liquid chromatograph, only a single peak was observed after 180 seconds. From these analytical values, it was found that the liquid (f) was a compound having the same structure as that of the liquid (e) obtained in Preparation 5.

PREPARATION 7

54 parts of DOP and 28 parts of commercial itaconic acid anhydride were put into a reaction vessel. After nitrogen replacement under reduced pressure, the reaction vessel was immersed into an oil bath of 150° C., and the reaction mixture was allowed to react by heating for 240 minutes under stirring. The reaction product was a viscous liquid, which when removed and cooled became a colorless, transparent, glassy solid having a softening point of 84°–88° C. Upon recrystallizing this substance from tetrahydrofuran/hexane (1:1), 72 parts of the object compound having the following structure:

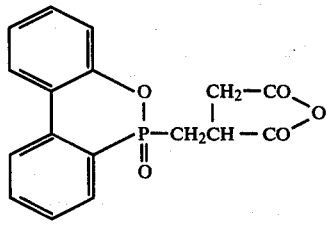

The purified product thus obtained was white needle-like crystals having a melting point of 187.4° C. The infrared spectrum of the crystals had a maximum absorption value at 2940, 1788, 1600, 1480, 1438, 1235, 1120, 1068, 914, 760, 720, 620 and 530 cm$^{-1}$, respectively. The elemental analysis values were P=9.42%, C=62.29% and H=4.14%, which showed a good coincidence with the theoretical values: P=9.44%, C=62.20% and H=3.99%.

PREPARATION 8

32.8 parts of the previously mentioned phosphorus compound (V) represented by the formula below, 31.0 parts of ethylene glycol and 0.04 part of potassium titanyl oxalate were supplied to an autoclave equipped with pressure and temperature regulating means. The reaction mixture was allowed to react under a nitrogen atmosphere in a temperature range of from 200° to 220° C. for 120 minutes under stirring. The pressure of the reaction system was then gradually reduced to 1 mm Hg in 60 minutes. Subsequently, the reaction mixture was reacted for 120 minutes at a temperature of 220° C. under a pressure below 1 mm Hg. The resulting product was a yellow solid having a softening point of 75° C. Its phosphorus content was 8.30%.

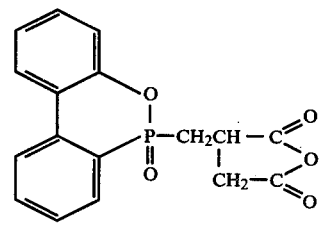

(v)

PREPARATION 9

35.8 parts of 9,10-dihydro-10-(1,2-dicarboxy) ethyl-9-oxa-10-phosphaphenanthrene-10-oxide, 31 parts of ethylene glycol and 0.04 part of potassium titanyl oxalate were supplied to the same autoclave as used in Preparation 8. The reaction mixture was allowed to react under a nitrogen atmosphere in a temperature range of from 160° to 240° C. for 120 minutes under stirring. The pressure of the reaction system was then gradually reduced to 1 mm Hg in 60 minutes. Subsequently, the reaction mixture was reacted at 240° C. under a pressure of 1 mm Hg for 60 minutes. The resulting product was a yellow solid having a softening point of about 30° C. Its phosphorus content was 8.90%.

PREPARATION 10

A mixture of 18.7 g. of 9,10-dihydro-10-(2,3-dimethoxycarbonyl)propyl-9-oxa-10-phosphaphenanthrene-10-oxide, 14.4 parts of 1,4-cyclohexane dimethanol and 0.02 part of ammonium titanyl oxalate was charged into the same autoclave as used in Preparation 8 and was reacted under a nitrogen atmosphere in a temperature range of from 200° to 250° C. for 90 minutes. The pressure of the reaction system was then gradually reduced to 5 mm Hg in 60 minutes. Subsequently, the mixture was reacted at 250° C. under a pressure of 5 mm Hg. The resulting product was a yellow solid having a softening point of 78° C. and its phosphorus content was 6.48%.

PREPARATION 11

18.7 parts of 9,10-dihydro-10-(1,2-dicarboxy)ethyl-9-oxa-10-phosphaphenanthrene-10-oxide, 8.7 parts of dimethyl phthalate, 24.8 parts of ethylene glycol, 0.01 part of zinc acetate and 0.02 part of potassium titanyl oxalate were supplied to the same reaction vessel as used in Preparation 8. The reaction mixture was reacted under a nitrogen atmosphere in a temperature range of from 150° to 240° C. for 200 minutes under stirring. The pressure of the reaction system was then gradually reduced to 1 mm Hg in 60 minutes. Subsequently, the reaction mixture was reacted at 250° C. under a pressure below 1 mm Hg for 100 minutes. The resulting product was a yellow solid having a softening point of 79° C. and its phosphorus content was 5.41%.

PREPARATION 12

32.8 parts of the phosphorus compound (q), 12.4 parts of ethylene glycol, 19.0 parts of 2,2-bis(3,5-dibromo-4-hydroxyphenyl)propane and 0.04 part of potassium titanyl oxalate were supplied to the same autoclave as used in Preparation 8. The reaction mixture was reacted under a nitrogen atmosphere in the temperature range of from 150° to 200° C. for 60 minutes, and then the pressure of the reaction system was reduced to 1 mm Hg in 80 minutes. Subsequently, the reaction mixture was reacted at 210° C. under 1 mm Hg for 120 minutes. The resulting product was a yellow solid having a softening point of 78° C. and its phosphorus content was 5.70% and the bromine content was 17.63%.

PREPARATION 13

570 g. of 6,8-dichloro-9,10-dihydro-9-oxa-10-phosphaphenanthrene-10-oxide was charged into a five-necked flask, 1000 ml in capacity, equipped with a thermometer, a gas introducing inlet, a gas vent, a charging inlet and a stirrer. While nitrogen gas was blown into the flask, the temperature of the content was raised. When the temperature reached 160° C., stirring was started. 260 g. itaconic acid was gradually added at this temperature. After the completion of the addition, the reaction was continued for a further period of 7 hours, whereby a pale yellow resinous reaction product was obtained. It was found by the analysis of infrared absorption spectrum that this reaction product is a compound having the following structure:

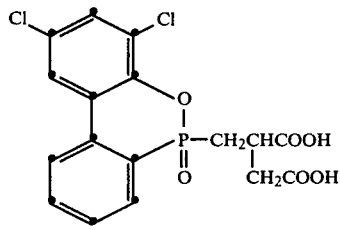

PREPARATION 14

576 g. of 2,6,8-tri-tert-butyl-9,10-dihydro-9-oxa-10-phosphaphenanthrene-10-oxide was charged into the same five-necked flask as used in Preparation 13. While nitrogen gas was blown into the flask, the temperature of the content was raised. At 150° C., 237 g. dimethyl itaconate was gradually added dropwise under stirring. After the completion of the addition, the reaction mixture was maintained at this temperature for a further period of 10 hours to complete the reaction. It was found by the analysis of infrared absorption spectrum that the reaction product was a compound having the following structure:

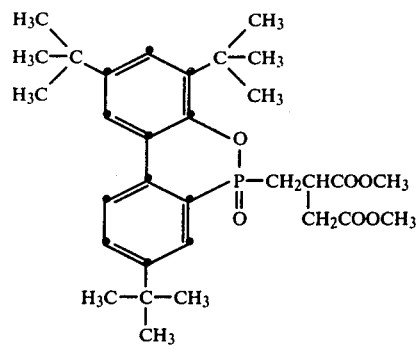

EXAMPLE 1

A mixture consisting of 388 parts of dimethyl terephthalate, 248 parts of ethylene glycol, 9.4 parts of the phosphorus-containing compound (b), 0.09% zinc acetate and 0.03% antimony trioxide based on the dimethyl terephthalate, was heated at 150°–230° C. for 120 minutes to perform transesterification reaction. Then the temperature of the reaction system was raised to 275° C. in 30 minutes and the pressure of the system was gradually reduced so that it reached 0.2 mm Hg after 45 minutes. The reaction was continued under this condition for a further period of 80 minutes. The intrinsic viscosity of the resulting polymer was 0.56, the melting point was 256° C. and the ratio of phosphorus remaining in the polymer was 97%. The flame retardancy was 5.1 times.

EXAMPLE 2

A polymer was obtained in the same way as in Example 1, except that 9.8 parts of phosphorus compound (m) was used in place of the phosphorus compound used in Example 1. The resulting polymer had an intrinsic viscosity of 0.54, a melting point of 255° C., and a remaining phosphorus ratio of 91%. The flame retardancy was 5.1 times.

COMPARATIVE EXAMPLE 1

Upon performing the transesterification reaction in the same way as in Example 1 except for using 10.2 parts of triphenyl phosphate in stead of the phosphorus compound used in Example 1, ethylene glycol began to distill out during the reaction to inhibit the completion of the reaction, so that it was impossible to produce the object polymer.

COMPARATIVE EXAMPLE 2

A mixture consisting of 388 parts of dimethyl terephthalate, 248 parts of ethyelene glycol, 0.03% zinc acetate and 0.03% antimony trioxide based on the dimethyl terephthalate was heated at 150°–230° C. for 120 minutes to perform transesterification reaction. 10.2 parts of triphenyl phosphate was added to this reaction system and the temperature of the system was raised to 270° C. in 30 minutes and the pressure of the system was gradually reduced. At this time, the viscosity arose sharply and the reaction mixture gelled. Therefore, the object polyester fiber could not be obtained.

COMPARATIVE EXAMPLE 3

A polymer was obtained in the same way as in Example 1 except that 8.1 parts of diethyl benzenephosphonate was used in stead of the phosphorus compound used in Example 1. The intrinsic viscosity of the obtained polymer was 0.59, the melting point was 256° C. and the remaining phosphorus ratio was 45%. The flame retardance was 3.2 times.

EXAMPLE 3

A mixture consisting of 388 parts of dimethyl terephthalate, 248 parts of ethylene glycol, 14.6 parts of the phosphorus compound (p), 0.07% zinc acetate, 0.02% potassium titanyl oxalate and 0.01% antimony trioxide based on the dimethyl terephthalate, was heated to 150°–230° C. to perform transesterification reaction. The temperature of this reaction system was raised to 275° C. in 30 minutes, and the pressure of the system was gradually reduced so that it reached 0.2 mm Hg after 45 minutes. Under this condition, the reaction was further continued for 60 minutes. The intrinsic viscosity of the resulting polymer was 0.61, the melting point was 254° C., and the remaining phosphorus ratio was 93%. The flame retardancy was 5.2 times.

EXAMPLE 4

A mixture consisting of 388 parts of dimethyl terephthalate, 248 parts of etheylene glycol, 5.7 parts of the phosphorus compound used in Example 1, 23 parts of 2,2-bis(3,5-dibromo-4-hydroxyethoxyphenyl)propane, 0.05 % zinc acetate and 0.05% antimony trioxide based on the dimethyl terephthalate, was heated at 150°–230° C. for 120 minutes to perform transesterification reaction. The temperature of the system was raised to 275° C. in 30 minutes and the pressure of the system was gradually reduced so that it reached 0.2 mm Hg after 45 minutes. Under this condition, the reaction was further continued for 100 minutes. The intrinsic viscosity of the resulting polymer was 0.59, the melting point was 250° C. and the remaining phosphorus ratio was 96%. The flame retardancy was 5.6 times.

EXAMPLE 5

A mixture consisting of 335 parts of terephthalic acid, 248 parts of ethylene glycol, 0.2 part of antimony trioxide and 1.0 part of triethylamine, was heated at 230° C. under 2.5 kg/cm² for 60 minutes. At this point of time, 10.3 parts of the phosphorus compound (s) was added, and the reaction was further continued under the condition of 230° C. and 2.5 kg/cm². The resulting reaction product was transferred to a reaction vessel for polycondensation. The temperature of the system was raised from 230° C. to 275° C. in 40 minutes, and the pressure was gradually reduced to 0.3 mm Hg finally. The reaction was further continued for 60 minutes under the condition of 275° C. and 0.3 mm Hg. The intrinsic viscosity of the resulting polymer was 0.59, the melting point was 254° C., and the remaining phosphorus ratio was 94%. The flame retardancy was 5.0 times.

EXAMPLE 6

The polymer obtained in Example 1 was spun in the usual way at a temperature of 290° C. and at a spinning speed of 300 m/min to obtain an undrawn yarn. The undrawn yarn was then drawn in the usual way at a hot pin temperature of 80°–85° C. to find the maximum drawing ratio until the yarn was broken. The maximum drawing ratio was found to be 6.1 times.

COMPARATIVE EXAMPLE 4

A mixture consisting of 388 parts of dimethyl terephthalate, 248 parts of ethylene glcyol, 7.4 parts of diethyl 2-ethoxycarbonylethylphosphonate, 0.09% zinc acetate, 0.02% potassium titanyl oxalate and 0.01% antimony trioxide based on the dimethyl terephthalate, was heated at 150°–230° C. for 120 minutes to perform transesterification reaction. Then the temperature of this system was raised to 275° C. in 30 minutes, and the pressure of the system was gradually reduced so as to reach 0.2 mm Hg after 45 minutes. Under this condition, the reaction was continued for an additional time of 35 minutes. The intrinsic viscosity of the resulting polymer was 0.56, the melting point was 256° C. and the remaining phosphorus ratio was 97%. The flame retardancy was 5.1 times. Upon drawing this polymer in the same way as in Example 6, the maximum drawing ratio was 5.7 times.

EXAMPLE 7

A mixture consisting of 500 parts of dimethyl terephthalate, 360 parts of ethylne glycol, 20.2 parts of the phosphorus-containing compound-containing liquid (E) obtained in Preparation (5), 0.045% zinc acetate and 0.05% antimony trioxide based on the dimethyl terephthalate, was charged into an autoclave and was heated at 150°–230° C. for 120 minutes to perform transesterification reaction. The temperature of the reaction system was raised to 275° C. in 30 minutes and the pressure of the system was gradually reduced so as to be 0.2 mm Hg after 45 minutes. Under this condition, the reaction was further continued for 60 minutes. The intrinsic viscosity of the resulting polymer was 0.636, the melting point was 257° C. and the remaining phosphorus ratio in the polymer was 99% (content 3025 ppm as phosphorus atom). This polymer was spun at 290° C. by means of an extruder-type spinning machine in the usual way. The fiber thus obtained was drawn 3.8 times the length on a hot plate at 87° C. in the usual way to obtain the final fiber, of which the strength was 5.6 g/d and the elongation was 36%. This fiber was knitted into a tricot and its flame retardancy was measured according to the flame retardancy standard (coil method) established by the Fire Services Act Enforcement Ordinance Section 4, Subsection 3, Paragraph 4 of Japan. The ignition time was five times. In comparison with the fact that the ignition time of the polyester fiber containing no phosphorus compound was below 2 times, this fiber had an excellent flame retardant effect.

EXAMPLE 8

A polymer was obtained in the same way as in Example 7 except that 21.9 parts of the liquid (F) obtained in Example 6 was used in place of the phosphorus-containing compound used in Example 7. The intrinsic viscosity of the resulting polymer was 0.629, the melting point was 258° C. and the remaining phosphorus ratio was 98%. The flame retardancy was 5.5 times.

EXAMPLE 9

A mixture consisting of 500 parts of dimethyl terephthalate, 360 parts of ethylene glycol 20.0 parts of the phosphorus compound (z), 0.045% manganese acetate and 0.02% amorphous germanium dioxide based on the dimethyl terephthalate, was charged into a reaction vessel and was heated at 150°–230° C. for 140 minutes to perform transesterification reaction. After 0.34 part of trimethyl phosphate was added to this reaction mixture, the temperature of this reaction system was raised to 275° C. in 40 minutes and the pressure of the system was gradually reduced so as to be 0.1 mm Hg after 40 minutes. Under this condition, the reaction was further continued for 95 minutes. The intrinsic viscosity of the resulting polymer was 0.601, the melting point was 257° C., and the ratio of phosphorus remaining in the polymer was 90%. The flame retardancy was 5.5 times.

EXAMPLE 10

A mixture consisting of 2500 parts of dimethyl terephthalate, 1600 parts of ethylene glycol, 0.04 weight % zinc acetate and 0.05 weight % antimony trioxide was subjected to transesterification reaction at 150°–230° C. for 120 minutes. The temperature of this reaction system was gradually raised and at the same time the pressure was gradually reduced so as to be 275° C. and 0.09 mm Hg, respectively, after 100 minutes at the end. The polymerization was continued for an additional time of 30 minutes. The intrinsic viscosity of the resulting polymer was 0.62, and the b value of the polymer measured by means of a Color Difference Meter 101-D produced by Nippon Denshoku Kogyo Co. was 3.0. The flame retardant obtained in Preparation 9 crushed into granules was mixed with pellets of this polymer by means of a blender so that the flame retardant granules form 6.2% by weight. The mixture was spun into filaments in the usual way by means of a melt-spinning apparatus at the spinning temperature of 285° C. at a spinning speed of 600 m/min. The intrinsic viscosity of the thus-obtained filaments was 0.55, and the phosphorus content was 0.4%. The filaments were drawn 4.6 times the length on a heated plate at 90° C. The thus-obtained drawn yarn was knitted into a tricot and the b value of the tricot measured in the same way was found to be 4.5. The flame retardancy was 5.0 times.

EXAMPLE 11

A mixture consisting of 2500 parts of dimethyl terephthalate, 1600 parts of ethylene glycol, 122 parts of 9,10-dihydro-10-(2,3-dimethoxycarbonyl)propyl-9-oxa-10-phosphaphenanthrene-10-oxide, 0.04 weight % zinc acetate and 0.05 wt % antimony trioxide, was subjected to transesterification reaction at 150°–230° C. for 140 minutes. Then the temperature of the reaction system was gradually raised and at the same time the pressure was gradually reduced so that the temperature and the pressure reached 275° C. and 0.09 mm Hg respectively after 100 minutes at the end. The polymerization was further continued for 67 minutes. The intrinsic viscosity of the resulting polymer was 0.60 and the b value was 6.1. In the same way as in Example 10, pellets of this polymer were spun into filaments and the filaments were drawn. The intrinsic viscosity of the filaments was 0.56 and the phosphorus content was 0.4%. The b value of a tricot from the filaments was 6.7. The flame retardancy of the tricot was 5.1 times.

EXAMPLES 12–17

Mixtures each consisting of 500 parts of dimethyl terephthalate, 360 parts of ethyelne glycol and the prescribed amount of each catalyst, based on the dimethyl terephthalate, shown in Table 1, were put into reaction vessels, respectively, and were subjected to transesterification reaction at 150°–230° C. for 120 minutes. To each of the reaction vessels, 46.5 parts of the phosphorus composition (the liquid (F)) obtained in Preparation 6 and the prescribed amount of each phosphorus compound as a stabilizer shown in Table 1 were added. Then the temperature of the reaction system was raised to 275° C. in 40 minutes and the pressure was gradually reduced so that it reached 0.1 mm Hg after 40 minutes. Under this condition, the reaction was further continued. The polymerization time and the characteristic values of each of the polymers thus obtained are shown in Table 1. The color tone (b value) of the polymer shown in Table 1 was measured from polymer pellets (0.8 mm × 4 mm) packed into a cell having a diameter of 40 mm and a height of 30 mm, by means of a Color Difference Meter 101-D produced by Nippon Denshoku Co. The transparency of the polymer upon being melted is also observed and the result is shown together in Table 1.

It is apparent from Table 1 that the addition of the phosphorus compounds as stabilizers, even in the presence of the phosphorus compound of the present invention, improves polymer color and transparency, and the flame retardancy of each polymer was 5.6–5.8 times, so that any lowering of flame retardancy by the addition of the stabilizers was not observed.

Table 1

| Example | Catalyst (parts) | Phosphorus compound (parts) | Polymerization time (min) | Intrinsic viscosity | Transparency | Color tone (b balue) |
|---|---|---|---|---|---|---|
| 12 | Zn acetate 0.175 Sb trioxide 0.25 | Diethyl 2-ethoxy-carbonylethylphosphonate 0.46 | 65 | 0.62 | Completely transparent | 5.2 |
| 13 | Zn acetate 0.17 Co acetate 0.02 Sb trioxide 0.25 | Diethyl 2-ethoxy-carbonylethylphosphonate 0.57 | 80 | 0.61 | " | 4.2 |
| 14 | Mn acetate 0.2 Sb trioxide 0.25 | Trimethyl phosphate 0.22 | 105 | 0.60 | " | 4.8 |
| 15 | Mn acetate 0.2 Ge dioxide 0.1 | Triphenyl phosphite 0.50 | 100 | 0.60 | " | 4.3 |
| 16 | Ca acetate 0.6 Ge dioxide 0.1 | Trimethyl phosphate 0.33 | 105 | 0.59 | " | 4.2 |
| 17 | Zn acetate 0.175 Sb trioxide 0.25 | — | 70 | 0.62 | Slightly turbide | 7.5 |

What is claimed is:

1. A flame retardant polyester having a phosphorus atom content of 500–50,000 ppm containing a flame-retarding amount of a phosphorus containing compound represented by the following general formula (I):

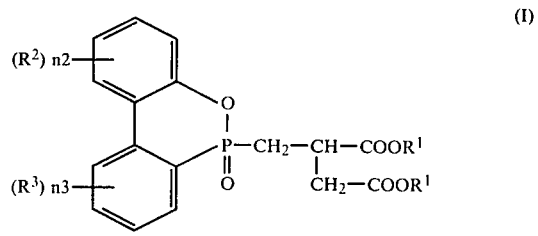

wherein each of $R^1$ is a hydrogen atom or hydrocarbon group having 1-10 carbon atoms which may contain a hydroxyl group, and both $R^1$'s may together form a dehydrated ring when both of $R^1$'s represent hydrogen atoms, each of $R^2$ and $R^3$ is a member selected from the group consisting of halogen atoms and hydrocarbon groups having 1-10 carbon atoms, and each of n2 and n3 is an integer of 0-4.

2. A flame retardant polyester as claimed in claim 1 obtained by reacting the phosphorus-containing compound represented by the general formula (I) with terephthalic acid or an ester-forming derivative, and at least one glycol selected from the group consisting of alkylene glycols whose carbon atom number is less than 5 and 1,4-cyclohexane dimethanol or the ester-forming derivatives thereof.

3. A flame retardant polyester as claimed in claim 1 obtained by reacting the phosphorus-containing compound represented by the general formula (I) with a dicarboxylic acid or an ester-forming derivative thereof and glycol represented by the following general formula:

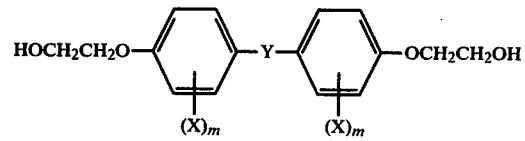

wherein X represents a halogen atom, Y represents an alkylidene group, cycloalkylidene group, arylalkylidene group, —S—, —SO—, —SO$_2$— or —O—, and m represents an integer of 1-4.

* * * * *